United States Patent
Lueck et al.

(10) Patent No.: US 9,575,023 B2
(45) Date of Patent: Feb. 21, 2017

(54) MEASURING APPARATUS AND METHOD FOR DETECTING FERROMAGNETIC PARTICLES

(71) Applicant: Rolls-Royce Deutschland Ltd & Co KG, Blankenfelde-Mahlow (DE)

(72) Inventors: Rudolf Lueck, Nuthetal (DE); Peter Hoehne, Fredersdorf (DE)

(73) Assignee: ROLLS-ROYCE DEUTSCHLAND LTD & CO KG, Blankenfel De-Mahlow (DE)

( * ) Notice: Subject to any disclaimer, the term of this patent is extended or adjusted under 35 U.S.C. 154(b) by 52 days.

(21) Appl. No.: 14/437,096

(22) PCT Filed: Oct. 21, 2013

(86) PCT No.: PCT/EP2013/071955
§ 371 (c)(1),
(2) Date: Apr. 20, 2015

(87) PCT Pub. No.: WO2014/064043
PCT Pub. Date: May 1, 2014

(65) Prior Publication Data
US 2015/0276641 A1 Oct. 1, 2015

(30) Foreign Application Priority Data
Oct. 22, 2012 (DE) ........................ 10 2012 219 242

(51) Int. Cl.
| | | |
|---|---|---|
| G01N 27/74 | (2006.01) | |
| G01R 33/12 | (2006.01) | |
| G01N 27/06 | (2006.01) | |
| G01N 15/06 | (2006.01) | |
| G01N 33/28 | (2006.01) | |
| G01N 15/00 | (2006.01) | |

(52) U.S. Cl.
CPC .......... G01N 27/06 (2013.01); G01N 15/0656 (2013.01); G01N 27/74 (2013.01); G01N 33/2858 (2013.01); G01N 33/2888 (2013.01); *G01N 2015/0053* (2013.01)

(58) Field of Classification Search
CPC . G01N 33/2858; G01N 15/0656; G01N 27/74
USPC .......................................................... 324/204
See application file for complete search history.

(56) References Cited

U.S. PATENT DOCUMENTS

| | | | |
|---|---|---|---|
| 4,100,491 A | 7/1978 | Newman et al. | |
| 4,127,808 A | 11/1978 | Sproul et al. | |
| 4,323,843 A | 4/1982 | Batham | |
| 5,179,346 A | 1/1993 | McGee et al. | |
| 5,406,208 A | 4/1995 | Bitts | |
| 5,742,234 A | 4/1998 | Owen | |
| 7,888,929 B2* | 2/2011 | Kordonski | B24B 1/005 324/204 |
| 2006/0125487 A1 | 6/2006 | Itomi | |
| 2010/0109686 A1* | 5/2010 | Zhe | G01M 13/02 324/698 |
| 2013/0087505 A1* | 4/2013 | Danov | B03C 1/0335 210/695 |

FOREIGN PATENT DOCUMENTS

| | | |
|---|---|---|
| DE | 19524353 | 1/1997 |
| DE | 69627742 | 3/2004 |
| DE | 102009022443 | 12/2010 |
| FR | 2443691 | 7/1980 |

OTHER PUBLICATIONS

English Translation of International Preliminary Report on Patentability dated Apr. 28, 2015 from counterpart App No. PCT/EP2013/071955.
German Search Report dated Jul. 1, 2013 for counterpart German Application No. 10 2012 219 242.5.
International Search Report dated Jan. 23, 2014 for PCT Application No. PCT/EP2013/071955.

* cited by examiner

*Primary Examiner* — Reena Aurora
(74) *Attorney, Agent, or Firm* — Shuttleworth & Ingersoll, PLC; Timothy J. Klima

(57) ABSTRACT

Measuring apparatus and measuring method for detecting ferromagnetic particles which are movably arranged in a liquid volume, characterized by a magnetic means for generating a magnetic field in the liquid volume, a measuring means for the total electrical resistance of the liquid volume with the ferromagnetic particles therein and a means for checking the function of the measuring apparatus with at least one low-value resistor of between 50 and 500Ω for carrying out a resistance measurement. The invention also describes a magnetic means with an electromagnet which, when in need of cleaning, can be demagnetized by means of correct energization (measured using the normal resistance measurement) and can be magnetized again when started up again.

19 Claims, 5 Drawing Sheets

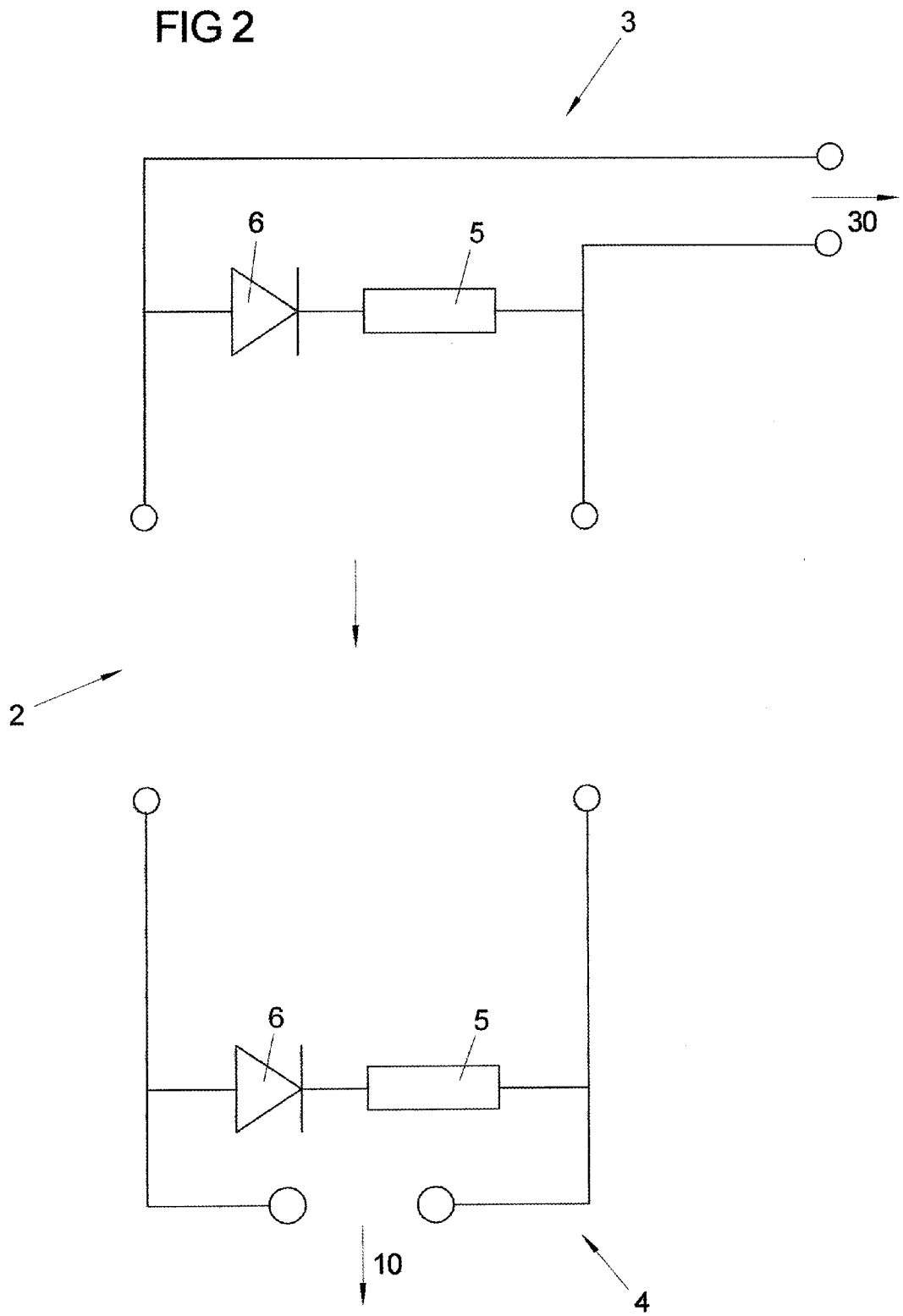

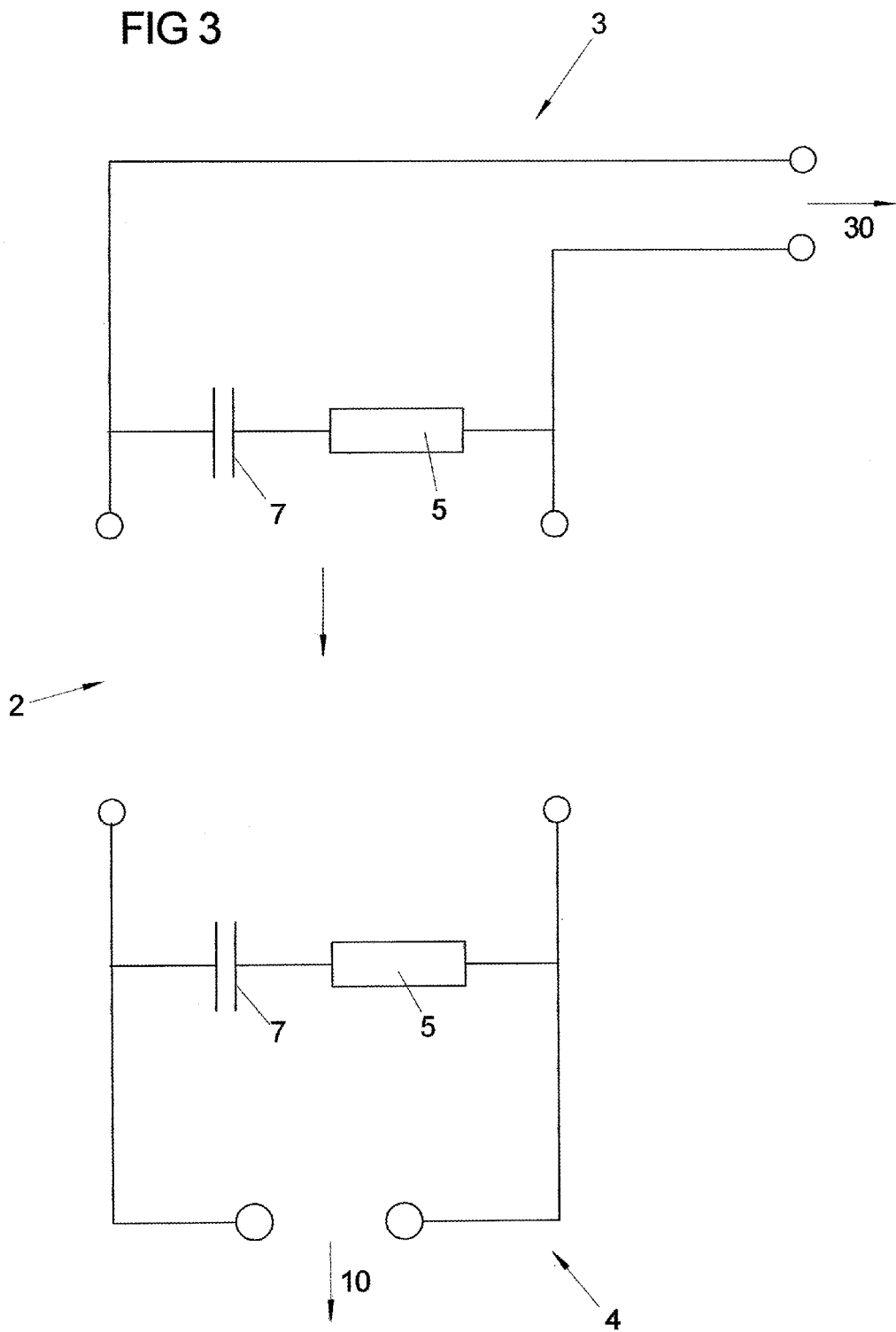

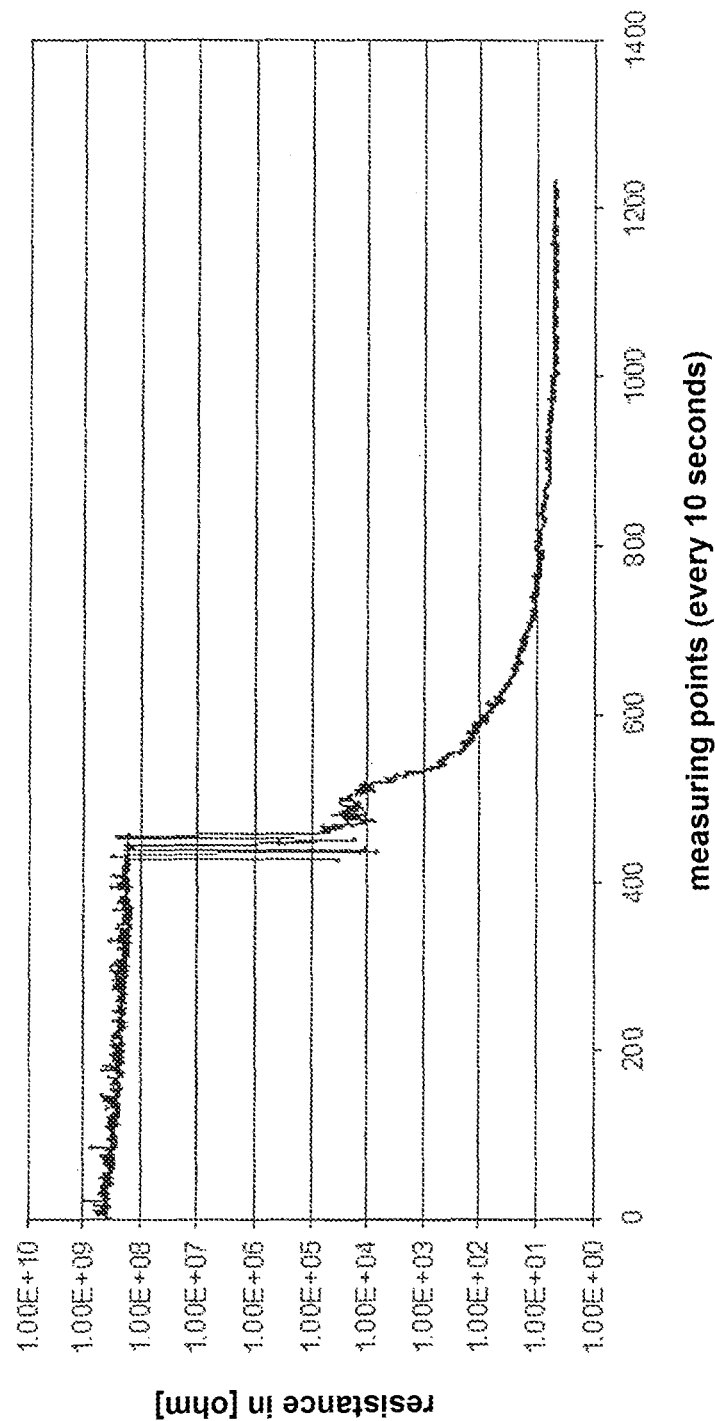

MEASURING APPARATUS AND METHOD FOR DETECTING FERROMAGNETIC PARTICLES

This application is the National Phase of International Application PCT/EP2013/071955 filed Oct. 21, 2013 which designated the U.S.

This application claims priority to German Patent Application No. DE102012219242.5 filed Oct. 22, 2012, which application is incorporated by reference herein.

The invention relates to a measuring apparatus for detecting ferromagnetic particles, as well as to a measuring method for detecting ferromagnetic particles.

During operation of mechanical devices such as aircraft engines, gears and pumps, for example, it repeatedly comes to the formation of metallic, especially ferromagnetic particles which may accumulate in liquids, such as in lubricants or in hydraulic fluid.

The accumulation of ferromagnetic particles (for example iron particles) may be a sign of a malfunction or of progressive wear in the device, which sooner or later leads to the device's failure. For example, the abrasion may lead to a blockage of valves.

Especially in devices in which safe operation has to be ensured on a permanent basis—such as in aircraft engines—it is problematic that the abrasion of ferromagnetic particles is not readily detectable from the outside. Per se known magnetic abrasion detectors (magnetic chip detectors) have a measuring range that is too small for the ferromagnetic particles.

Therefore, there is the objective to develop an efficient and reliable device for determining ferromagnetic abrasion.

The objective is achieved by a measuring apparatus having features as described herein.

Here, the ferromagnetic particles are present in a liquid volume, wherein a magnetic means serves for the generation of a magnetic field inside the liquid volume.

A measuring means for the electrical resistance of the liquid volume with the ferromagnetic particles contained therein detects the total electrical resistance, which particularly changes as the concentration of the ferromagnetic particles attached to the contacts of the EMCD (electric magnetic chip detector) increases. Further, a means for testing the function of the measuring apparatus has at least one low-ohm resistance between 50 and 500Ω for performing a resistance measurement. Thanks to the "on/off-switchability" of the resistors by reversing the polarity of the AC-DC voltage, a function test is ensured, which does not have any adverse effect on the sensitivity of the measurement, thus making it possible to detect very small ferromagnetic particles.

The ferromagnetic particles are arranged along the magnetic field lines inside the liquid volume. As the ferromagnetic particles form bridges between the magnetic poles, it comes to a change in the total resistance of the liquid volume, which allows statements about the presence as well as about the temporal development of the metallic abrasion.

According to the invention, the means for functional testing is configured with passive circuit elements, so that the reversal of the polarity of a DC voltage or the application of an AC voltage to said means for functional testing generates a signal to indicate a correct function and/or a malfunction of the measuring apparatus.

Thus, in an advantageous embodiment, the means for functional testing can comprise a plug connection, in which a first plug element can be connected to a measuring probe for the liquid volume and a second plug element can be connected to a measuring means for the electrical resistor, wherein the first and the second plug element each comprise a series connection of an electrical resistor with a diode.

In another embodiment, the means for functional testing has a plug connection, in which the first plug element can be connected to a measuring probe for the liquid volume, and the second plug element can be connected to a measuring means for the electrical resistor, wherein the first and second plug element respectively comprise a series connection of a capacitor with an electrical resistor. In these embodiments, a simple functional test can be carried out by switching from DC to AC.

It is advantageous when the measurement of the total electrical resistance is carried out through the liquid volume in a liquid-filled line with ferromagnetic particles arranged therein, particularly in a lubricant or an oil line. For detection of abrasion it is particularly advantageous when the ferromagnetic particles are arranged in a lubricant or oil line that is coupled to a roller bearing, particularly one having ceramic rolling elements, a gear and/or a pump.

Additionally or alternatively, it is advantageous when the ferromagnetic particles are arranged in front of a filter inside a recirculation conduit for a lubricant, and in particular for an oil, a coolant, a hydraulic fluid or a fuel, since this is where the detection of metallic particles is of particular importance.

Advantageously, the measuring apparatus is configured and designed in such a manner that particles with an average diameter of less than 40 µm, particularly less than 20 µm, and even more particularly less than 10 µm can be measured.

As the abrasion is forming, the electrical resistance varies within a wide range, so that it is advantageous if the measuring range of the total electrical resistance of the liquid volume with the ferromagnetic particles lies between 1 and 1010Ω.

In the process of determining the total electrical resistance in the liquid volume, it is also advantageous if a signal, particularly a warning signal, about a malfunction can be triggered in the event that the total electrical resistance falls below a predetermined threshold value. In this way, a measurement of the temporal development of the total electrical resistance during the operation of a device can serve for switching the device off in time, for example.

Preferably, the means for generating the magnetic field in the liquid volume comprises a permanent magnet and/or an electromagnet.

Further, it is advantageous to provide a mechanical device, in particular an aircraft engine, a gear, a rolling bearing or a pump with such a measuring apparatus.

It is also advantageous if the magnetic means for generating the magnetic field comprises an electromagnet, which can be selectively magnetized or demagnetized. In this manner, e.g. a zeroing of the measuring means can be performed in operation, and also cleaning can be facilitated.

In an advantageous embodiment, the temporal development, particularly the gradient of the resistance, can be detected over time by means of the measuring means for determining the electrical resistance. Through this detection of the continuous development of the signal via the change of resistance, a significant enhancement of the information content is achieved, since the increment (decrease of resistance over time) as well as the gradation of the increase is discernible (step height).

The object is also achieved by a method for detecting ferromagnetic particles in a liquid volume, wherein the temporal development of the total electrical resistance in a device is detected by means of the measuring means for the total electrical resistance of the liquid volume with the metallic particles contained therein. Here, a signal, particularly a warning signal, about a malfunction is triggered during the monitoring of the temporal development depending on a predetermined threshold value.

In an advantageous embodiment, the magnetic means for generating a magnetic field comprises an electromagnet with a ferromagnetic core, wherein the current is switched off for the purposes of cleaning, and demagnetization of the core is carried out at AC current of decreasing amplitude. In this manner it is also possible to magnetize the ferromagnetic core before the electrical current is switched off in order to ensure that the ferromagnetic particles may be removed after the current has been switched off.

The invention is explained in connection with the embodiments shown in the figures. Herein:

FIG. 2 shows a schematic representation of a first embodiment of a wiring for a plug connection;

FIG. 3 shows a schematic representation of a second embodiment of the wiring for a plug connection;

FIG. 4 shows a representation of a measurement of a total resistance in a liquid volume;

Figure 1:
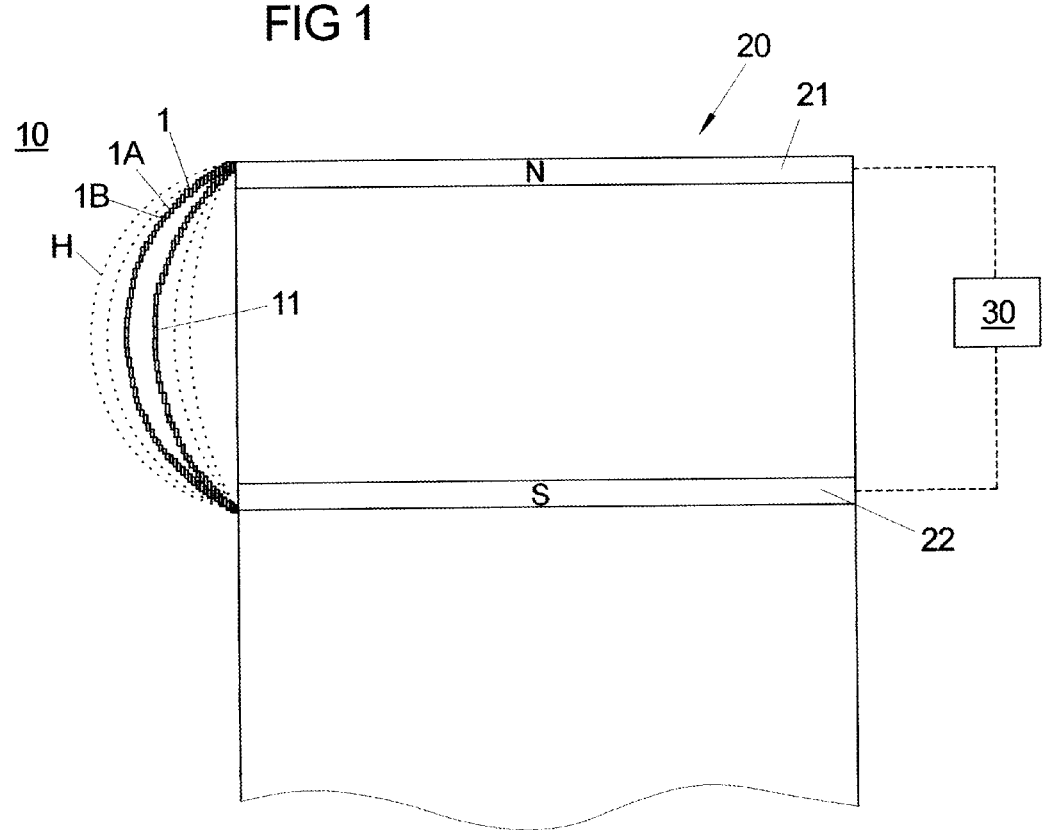
FIG. 1 shows a schematic representation of a measurement in a liquid line with ferromagnetic particles over a magnet, connecting the electrical contacts.
Figure 1A:
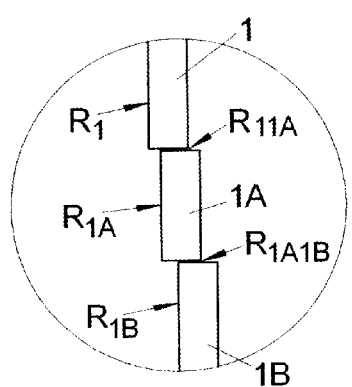
FIG. 1A shows an enlarged section of ferromagnetic particles attached to each other in the magnetic field inside a liquid volume according to FIG. 1.

In FIG. 1, a line 10 that is filled with lubricating oil is shown as a liquid volume, in which ferromagnetic particles 1, 1A, 1B (e.g. iron or steel particles) are present (see enlarged representation in FIG. 1A). Alternatively, such ferromagnetic particles 1, 1A, 1B can also collect in hydraulic lines.

Such ferromagnetic particles 1, 1A, 1B can form as a result of normal abrasion or of damage to a device, which is not shown herein. Thus, broken-off material at a ceramic rolling element, e.g. in a hybrid roller bearing (metal guide tracks with ceramic balls or rollers) may result in damage to the metallic guide tracks of the rolling element. In this manner, ferromagnetic particles 1, 1A, 1B can enter the lubricant circulation and thus the liquid volume of a line 10.

If a magnetic field H is applied to the liquid in the line 10 by using a magnetic means 20, the ferromagnetic particles 1, 1A, 1B are arranged along field lines between the magnetic poles 21, 22 in the liquid volume of the line 10. Generally, a magnetic means 20 can be understood to be a bar magnet which protrudes into the liquid 10. From the constructional standpoint, this can be solved by screwing in such a bar magnet into an oil duct or a hydraulic line by using a sleeve, for example. On the side that is facing away from the liquid 10, lines are arranged which transfer measuring signals from the liquid 10, e.g. to a measuring means 30 for determining electrical resistance.

Starting from a certain number of ferromagnetic particles 1, 1A, 1B, the ferromagnetic particles 1, 1A, 1B are arranged along magnetic field lines H inside the liquid 10 in the form of chains, so that electrically conducting bridges 11 are created, as is schematically shown in FIG. 1. If the total electrical resistance or the electrical conductivity of the content of line 10 is now measured with the measuring means 30, the formation of the bridges 11 can be detected, as the electrical resistance decreases (or the conductivity increases).

The total electrical resistance of the bridge 11 is comprised of the ohmic resistance R1, R1A, R1B of the individual ferromagnetic particles 1, 1A, 1B and the transition resistances R11A, R1A1B present between the ferromagnetic particles 1, 1A, 1B etc. In those contacts that are not yet completely bridged with ferromagnetic particles, the current flows through the liquid, which, however, takes place at a much higher resistance.

With the embodiment described herein it is possible to measure the change in the electrical resistance (see FIG. 4) through the formation of very small ferromagnetic particles 1, 1A, 1B (particularly smaller than 50 μm). Here, the ferromagnetic particles 1, 1A, 1B are formed along a magnetic field H. In the embodiments described herein, the ferromagnetic particles 1, 1A, 1B can be almost indefinitely small. The limit is at the point where the effective magnetic force becomes smaller than the resisting force. The resisting force is given by the surface of the ferromagnetic particle 1, 1A, 1B, the viscosity of the liquid (e.g. an oil) and the velocity of the ferromagnetic particle 1, 1A, 1B, caused by the magnetic force acting in the direction of the magnet. The ferromagnetic particles 1, 1A, 1B have to reach the magnet in the time (attraction of the particle through the liquid) in which the particle moves past the magnet. The relation of the effective magnetic mass to the effective surface of the particle is relevant here, as are the velocity of the oil flow and the viscosity of the oil.

In FIG. 2, a first embodiment of the wiring of a plug connection 3 is shown in a schematic representation, which is embodied as a means 2 for the functional testing of the measuring apparatus for detecting ferromagnetic particles 1, 1A, 1B. At that, the plug element 3 is assigned to the measuring means 30 for detecting the electrical resistance. A measurement of the electrical resistance in the liquid volume is carried out through the second plug element 4.

Here, the two plug elements 3, 4 of the means 2 for functional testing are provided with passive electronic components, in this case with an electrical resistor 5 and a diode 6, respectively. Functional testing of this first embodiment is carried out through a polarity reversal of a DC voltage. The diode 6 only works in one direction in the forward direction, so that at one time a very high resistance (off-state resistance) and at another time only the on-state resistance of the diode is present in addition to the ohmic resistance in the plugs 3, 4.

During the measuring operation, the diode 6 is operated in high-resistance direction, so that the resistance in the plug elements 3, 4 does not play any role. The plug connection thus facilitates an exact measurement within a very large resistance range, as is documented by the exemplary measurement curve of FIG. 4. In the measurement up to the measuring point 400 the current flows via the liquid. The electrical conductivity changes perceivably as the particle adhesions at the north and the south pole 21, 22 of the magnetic means 20 are growing together. In this case, the electrical current is going to partially flow in the liquid (see FIG. 4, up to the measuring point 400). When the particle covers at the north and south pole 21, 22 of the magnetic means 20 touch each other, the resistance between the electrical contacts decreases by several decades.

At the measuring point 420, the attached metal particles from north and south pole start touching each other and the current flows via the ferromagnetic particles and the transition resistance between the particles 1, 1A, 1B.

The electrical resistance measured in the liquid volume 10 results from the sum of the individual electrical resistances RA, RAA1, RA1, R1A1B, R1B of the ferromagnetic particles 1, 1A, 1B etc., wherein the ferromagnetic particles 1, 1A, 1B are arranged between the magnetic poles 21, 22 in the manner of a conductive bridge 11, as well as from the resistance via the liquid (measuring points 0 to 400) before the bridge is fully formed over the contacts.

The second embodiment according to FIG. 3 works in a similar manner. However, here the plug elements 3, 4 are respectively provided with resistors 5 and capacitors 7 which are connected in series. In the assembled state, a series connection of respectively one resistor 5 and one capacitor 7 is present in the plug connection.

Here, the functional test is carried out by switching to an AC voltage. At that, the complex resistance, consisting of the resistors 4 and the capacitors 7, is visible.

In the measuring operation at DC voltage, the measured resistance reflects the total resistance of the ferromagnetic particles 1, 1A, 1B in the liquid volume 10. Hereby, too, very exact measurements can be carried out throughout a large resistance range.

The following cases of errors can be examined with the described embodiments of the means 2 for functional testing, for example:

1. Faulty Plug Connection 3, 4

In a plug element 3, 4 that is not plugged in or not plugged in completely, a resistance measurement yields the simple resistance value. In plugged-in plug elements the result is a halved resistance (provided resistances are the same).

2. Cable Break in the Measurement Line

The electrical resistance measured when a cable break is present is much higher than the test resistance from the parallel connection of the resistors.

3. Short-Circuit to Ground of the Measurement Line

The measured resistance is much smaller than the test resistance from the parallel connection of the resistors.

The embodiments described herein are also suitable for those cases where it can be assumed that only few particles connect the contacts in series over the magnetic poles 21, 22. This is especially important when very fine abrasion has to be expected, like in bearings, gears, pumps and the like.

With per se known EMCDs (electric magnetic chip detectors) it was possible to detect a sufficient electrical resistance only relatively late. In contrast, the embodiments described above can provide a reliable indication of ferromagnetic particles 1, 1A, 1B already at an early stage. One of the reasons for this is the protective circuitry that has been used so far in the known EMCDs. Among other things, this protective circuitry contains a low resistance in the EMCD itself (parallel to the contacts) as well as a low resistance at the plug elements (parallel to the contacts) to the EMCD. The low total resistance is then parallel to the sum of resistance of the ferromagnetic particles 1, 1A, 1B at the contacts over the magnetic poles 21, 22 of the EMCDs. This leads to high sums of resistance not being detectable over the contacts in the parallel connection. It is for this reason that resistance measurements are not carried out in the devices known so far.

The embodiments shown herein also facilitate the operation of a method for detecting ferromagnetic particles 1, 1A, 1B, in which the decrease of resistance is measured. It is to be expected that the resistance decreases significantly with a progressive absorption of electrically conductive ferromagnetic particles 1, 1A, 1B. Repeated measurements, an example for which is illustrated in FIG. 4, show that, when breaking out from a ball occurs, the resistance decreases from 200 MΩ to 25 kΩ within approximately 13 minutes. As a result, a continuous decrease and an asymptotic approximation to the resistance of 4Ω take place.

In one embodiment, a warning signal can be automatically generated if the resistance falls under a certain value, as a considerable amount of abrasion material has to be expected in the liquid volume 10.

Figure 5:
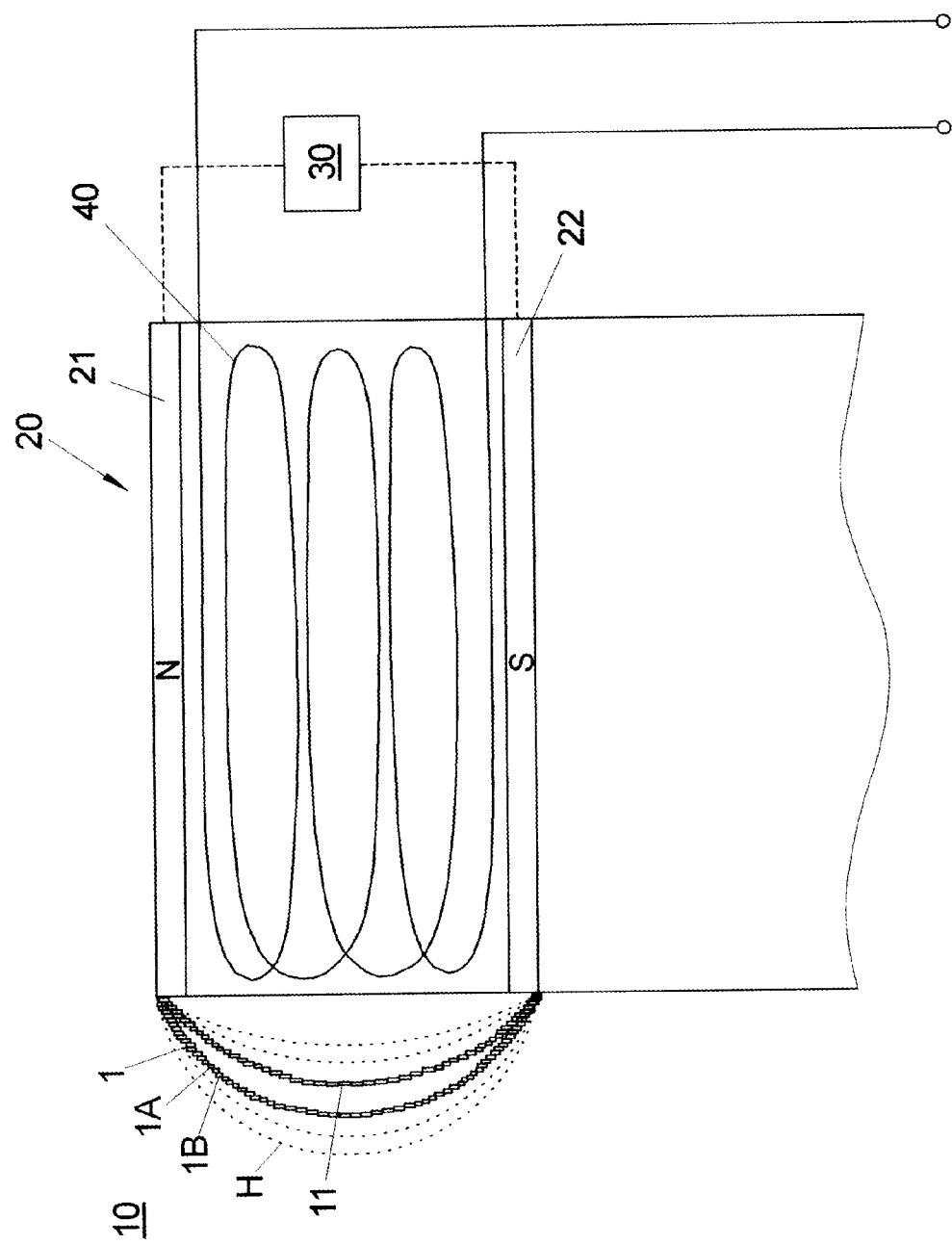
FIG. 5 shows an embodiment of a measuring apparatus with an electromagnet.

Another embodiment is shown in FIG. 5. Here, a magnetic means 20 with an electromagnet is used in the measuring apparatus. This has the advantage that the electromagnet can be switched off when it is fully covered by ferromagnetic particles 1, 1A, 1B (i.e. when a small electrical resistance is present). In addition, it is possible to demagnetize the residual magnetism from the ferromagnetic core in the electromagnet. This is done by applying an AC voltage with steadily decreasing amplitude.

As the core material 40 for the electromagnet, a medium-hard magnetic material is suitable. This combines the advantages that magnetism can be maintained and that demagnetization is possible without any problems.

In this manner, it becomes possible to switch off and demagnetize an EMCD that is fully covered by ferromagnetic particles. In this way, a "zeroing" of the measuring apparatus can be performed again after the full covering has occurred, making any manual cleaning unnecessary in the event that a full covering is indicated. The measurement can thus be carried out for any desired time, even during the flight.

If, for example, ferromagnetic particles from the EMCD are to be removed after the engine has been switched off, a higher current can be applied to the EMCD before the current is switched off, which would lead to a permanent magnetization of the medium-hard core material and thus would hold the particles until their manual removal.

PARTS LIST 1 ferromagnetic particles
2 means for functional testing
3 first plug element
4 second plug element
5 resistor
6 diode
7 capacitor
10 liquid volume, line with liquid
11 conductive bridge of ferromagnetic particles
20 magnetic means for creating a magnetic field
21 magnetic north pole
22 magnetic south pole
30 measuring means for determination the electrical resistance
40 core of an electromagnet
H magnetic field

The invention claimed is:

1. A measuring apparatus for detecting ferromagnetic particles which are arranged in a moveable manner in a liquid volume, comprising magnetic means for generating a magnetic field inside the liquid volume, measuring means for a total electrical resistance of the liquid volume with the ferromagnetic particles contained therein, and means for functional testing of the measuring apparatus with at least one low-ohm resistor between 50 and 500Ω for carrying out a resistance measurement, wherein the means for functional testing are formed with passive circuit elements in such a manner that reversing the polarity of a DC voltage or application of an AC voltage to the means for functional testing generates a signal in order to signalize a correct function or a malfunction of the measuring apparatus.

2. The measuring apparatus according to claim 1, wherein the means for functional testing comprise a plug connection which has a first plug element that can be connected to a measuring probe for the liquid volume, and has a second plug element that can be connected to a measuring means for the electrical resistance, wherein the first and the second plug element respectively comprise a series connection of the at least one electrical resistor with a diode.

3. The measuring apparatus according to claim 1, wherein the means for functional testing has a plug connection which has a first plug element that can be connected to a measuring probe for the liquid volume, and has a second plug element that can be connected to a measuring means for the electrical resistance, wherein the first and the second plug part respectively comprise a series connection of a capacitor with at least one electrical resistor.

4. The measuring apparatus according to claim 1, wherein the measurement of the electrical resistance is carried out through the liquid volume in a line filled with liquid with the ferromagnetic particles arranged therein, wherein the line is a lubricant or oil line.

5. The measuring apparatus according to claim 4, wherein, for detecting abrasion, the ferromagnetic particles are arranged in a lubricant or oil line which is coupled with at least one chosen from a roller bearing, a gear and a pump.

6. The measuring apparatus according to claim 4, wherein the ferromagnetic particles are arranged in front of a filter inside a recirculation conduit for at least one chosen from a lubricant, hydraulic fluid, fuel and coolant.

7. The measuring apparatus according to claim 1, wherein the measuring apparatus is configured and designed to measure particles with an average diameter of less than 40 µm.

8. The measuring apparatus according to claim 1, wherein the measuring range of the total electrical resistance of the liquid volume (10) is between 1 and $10^{10}\Omega$.

9. The measuring apparatus according to claim 1, wherein in determining of the total electrical resistance of the liquid volume, in an event that it falls below a predetermined threshold value, a warning signal about a malfunction can be triggered.

10. The measuring apparatus according to claim 1, wherein the means for generating the magnetic field in the liquid volume comprises at least one chosen from a permanent magnet and an electromagnet.

11. The measuring apparatus according to claim 1, wherein the magnetic means for generating the magnetic field comprises an electromagnet, which can be selectively magnetized or demagnetized.

12. The measuring apparatus according to claim 1, wherein, with the measuring means for determining the electrical resistance, a gradient of the resistance can be detected over time.

13. A mechanical device, the mechanical device being one chosen from an aircraft engine, a gear, a rolling bearing and a pump, comprising the measuring apparatus according to claim 1.

14. The measuring apparatus according to claim 1, wherein the measuring apparatus is configured and designed to measure particles with an average diameter of less than 20 µm.

15. The measuring apparatus according to claim 1, wherein the measuring apparatus is configured and designed to measure particles with an average diameter of less than 10 µm.

16. A method for detecting ferromagnetic particles in a liquid volume, comprising:
   providing a measuring apparatus for detecting ferromagnetic particles which are arranged in a moveable manner in a liquid volume, the measuring apparatus comprising:
      magnetic means for generating a magnetic field inside the liquid volume,
      measuring means for a total electrical resistance of the liquid volume with the ferromagnetic particles contained therein, and
      means for functional testing of the measuring apparatus with at least one low-ohm resistor between 50 and 500Ω for carrying out a resistance measurement,
      wherein the means for functional testing are formed with passive circuit elements in such a manner that reversing the polarity of a DC voltage or application of an AC voltage to the means for functional testing generates a signal in order to signalize a correct function or a malfunction of the measuring apparatus,
   wherein, with the measuring means for the total electrical resistance of the liquid volume with the ferromagnetic particles contained therein, a temporal development of the total electrical resistance is detected.

17. The method according to claim 16, wherein a warning signal about a malfunction is triggered during the monitoring of the temporal development depending on a predetermined threshold value.

18. The method according to claim 16, wherein the magnetic means for generating the magnetic field comprises an electromagnet with a ferromagnetic core, wherein the current is switched off for the purposes of cleaning, and demagnetization of the core is carried out with an AC current of decreasing amplitude.

19. The method according to claim 18, wherein when an electromagnet with a ferromagnetic core is used, the ferromagnetic core is magnetized before the electrical current is switched off in order to ensure that the ferromagnetic particles are removed after the current has been switched off.

* * * * *